United States Patent [19]
Pescetti

[11] 3,939,259
[45] Feb. 17, 1976

[54] COATING COMPOSITION AND THERAPEUTIC PREPARATION INCORPORATING SAME

[76] Inventor: Anthony Pescetti, 999 E. Mission Road, Fallbrook, Calif. 92028

[22] Filed: May 24, 1974

[21] Appl. No.: 473,289

[52] U.S. Cl. .................... 424/20; 424/19; 424/34; 424/36; 424/37
[51] Int. Cl.² ......................................... A61K 9/22
[58] Field of Search .............................. 424/19–23, 424/31–38

[56] References Cited
UNITED STATES PATENTS

| | | | |
|---|---|---|---|
| 2,928,770 | 3/1960 | Bardani | 424/21 |
| 2,953,497 | 9/1960 | Press | 424/20 |
| 2,996,431 | 8/1961 | Barry | 424/20 X |
| 3,080,294 | 3/1963 | Shepard | 424/20 |
| 3,115,441 | 12/1963 | Hermelin | 424/34 X |
| 3,344,029 | 9/1967 | Berger | 424/34 X |
| 3,365,365 | 1/1968 | Butler et al. | 424/20 X |
| 3,524,756 | 8/1970 | Signorino et al. | 117/72 |
| 3,576,663 | 8/1971 | Signorino et al. | 117/72 |
| 3,738,952 | 6/1973 | Signorino et al. | 260/27 |
| 3,741,795 | 6/1973 | Signorino et al. | 117/100 |

Primary Examiner—Shep K. Rose
Attorney, Agent, or Firm—Fulwider Patton Rieber Lee & Utecht

[57] ABSTRACT

A therapeutic preparation consisting of particles containing a therapeutically active material are coated with a disintegratable coating comprising zein and shellac. A first group of particles contains no coating or a coating subject to rapid disintegration upon ingestion to release an initial dose of therapeutic material and remaining groups of particles are coated with increasingly thicker coatings for delayed disintegration to release subsequent doses of therapeutic material. The coating composition may include disintegration modifiers so that thinner coatings of the zein-shellac coating material can be employed than would be required for zein shellac alone to obtain the delayed disintegration of the coating.

2 Claims, No Drawings

COATING COMPOSITION AND THERAPEUTIC PREPARATION INCORPORATING SAME

The therapeutic preparation is formed by placing a portion of uncoated particles in a revolving pan and contacting the particles with sufficient amount of zein-shellac solution to cover the pellets. This is followed by a drying operation. The coating operation is repeated several times until the coating thickness is such as to resist disintegration for a selected period of time after ingestion. A portion of the coated particles is segregated and the coating procedure repeated until the coating thickness is such that the coating will resist disintegration and release the therapeutic material for absorbtion in the patient's system subsequent to the segregated portion of the particles.

The therapeutic preparation may be utilized as a mixture of groups of pellets in a capsule or the groups of pellets may be compressed into tablet form.

BACKGROUND OF THE INVENTION

This invention relates to therapeutic preparations in capsule or tablet form, and more particularly relates to such therapeutic preparations comprising particles having coatings thereover which are adapted to disintegrate at different times in the system of a patient thereby to provide for the timed release of a therapeutic material.

Timed disintegration capsules and tablets for the sequential, timed release of medicinal substances into a patient's system are well known in the art. Generally such capsules or tablets consist of particles containing the medicinal substance to be introduced into the system, and a coating over the particles of a material which is resistant to disintegration for a selected period of time. Such coating compositions are also referred to as enteric coating compositions, that is, compositions which are generally resistant to disintegration in the stomach, but which will disintegrate in the intestine. Enteric compositions also include compositions which are disintegratable so slowly in the stomach that the medicinal substance is not released until the capsule or tablet has reached the intestine of the patient. For example, coatings comprising bees wax and glyceryl monostearate; bees wax, shellac and cellulose; and cetyl alcohol, mastic and shellac have been proposed for use as slow release or timed release coatings for medicinal substances. Release of the medicinal substance by disintegration of the coating is generally controlled by controlling the thickness of the coating or by varying the coating composition.

The prior art compositions have generally proved deficient in that the medicinal substance is released so slowly in the system as to never reach the desired dosage level. Also, with many patients, the coatings are not disintegrated to the extent necessary to release the medicinal substance until the tablet or capsule has reached the colon and the medicinal substance is discharged from the system rather than absorbed by the intestine. Many prior art coating systems are not amenable to being formed into tablets or require the use of additive materials before the tableting operation, thereby raising the cost of manufacture.

The present invention, which also lies in the general area of timed disintegration coatings, represents a substantial improvement over the prior art compositions in that the time of disintegration is readily controllable and easily adjusted for release of a medicinal substance. In addition, the coating composition of the present invention may be utilized in tableting operations as well as in encapsulated therapeutic preparations.

SUMMARY OF THE INVENTION

The present invention resides in new and improved time releasable therapeutic preparations and in the method of manufacture thereof. More particularly, the improvement resides in a coating composition applied over particles containing a therapeutic substance to provide a coating thereover which is accurately and reproducibly disintegration resistant both in the stomach and in the intestinal tract for a selected period of time.

The coating composition comprises a mixture of zein and shellac which unexpectedly forms a coating which is selectively modified to resist disintegration for as short a period as approximately 20 minutes up to approximately eight hours. Disintegration of the coating results in the release of the therapeutic material for absorption into the patient's system. In the preferred embodiment, minor proportions of disintegration modifying materials are incorporated into the coating composition to reduce the total coating thickness for coatings designed to resist disintegration for substantial periods of time.

The therapeutic particles are coated with the zein-shellac coating composition of the present invention by contacting the particles with the coating composition in a substantially volatile solvent followed by a drying operation to remove the solvent. The coating operation is repeated until the zein-shellac coat thickness is built up to sufficient thickness for disintegration resistance for a desired period of time. By combining particles having different thickness of coatings into capsules and tablets, a therapeutic preparation is formed which, when ingested by a patient, will release doses of therapeutic materials at predetermined time intervals.

Other objects and advantages of the present invention will become apparent upon consideration of the following detailed description of the invention, and the novel features will be particularly pointed out in connection with the appended claims.

DETAILED DESCRIPTION OF THE INVENTION

The present invention is embodied in a therapeutic preparation in dosage unit form and its method of preparation, wherein groups of particles containing therapeutic substances are coated with a coating composition comprising zein and shellac. The coating thickness of each of the groups of particles is varied so that the coating is disintegrated in the patient's system at differing times after ingestion of the preparation of the present invention. In this manner, the therapeutic substances are released for absorption into the patient's system at controllably spaced time periods. In accordance with this invention, the dosage unit form of the therapeutic preparation comprises, in tablet or capsule form, groups of particles, each group of particles containing sufficient therapeutic material to comprise a dosage unit. The dosage unit will vary with the therapeutic material and the size and weight of the patient in accordance with standard practice.

As is conventional in the art, neutral particles utilized in the present invention are formed from a sugar and starch mixture in corn syrup or a starch and simple syrup mixture as described in the U.S. Pharmacopoeia.

The proportion of sugar to starch may range from between about 50% to about 90% sugar with the remainder of the composition being starch. The particles are formed in the conventional manner to a particle size of between about 12 mesh and about 40 mesh; with preferably an average particle size of about 24 mesh.

The therapeutic material may be incorporated directly in the neutral particle during formation thereof or may be dusted or otherwise distributed over the particles. When utilizing the latter method of applying the therapeutic material, it is preferred to apply a thin coating of a sealant material such as, for example, zein in order to bind the therapeutic material to the individual particles. In addition, one or more coats of the zein-shellac coating compositions may be applied to separate individual therapeutic materials or to act as a sealing coat. In such a case the coating composition is adjusted for rapid disintegration in the patient's system.

The particular therapeutic material utilized in the preparation of the present invention is not critical and may be selected from a wide variety of medicinal materials such as, for example, vitamins, minerals, sedatives, somniferics, drugs, analgesics antibiotics, sympathomimetics, cardiotonics and the like with therapeutically effective results. Moreover, combinations of different therapeutic materials, including those which are normally incompatible with each other, may be incorporated in the preparation of this invention. In the latter case, the different therapeutic materials are applied in separate layers on the particles and are separated from adjacent layers of therapeutic materials by a layer of the coating composition described hereinafter.

The timed release coating composition utilized to coat the particles of the therapeutic preparation of the present invention comprises a mixture of zein and shellac. Zein is the alcohol soluble proteinaceous derivative from corn gluten and is commercially available as a finely divided powder. White shellac is derived from the exudation of the insect *Laccifer lacca* which is formed while the insect is feeding on resiniferous host trees. The exudation is treated to remove natural dyes and following melting and straining, the product is bleached with sodium hypochlorite to remove remaining color bodies.

The zein and shellac composition comprise a major proportion of the coating composition used in the present invention, although minor proportions of disintegration modifiers or plasticizers may also be present. In the preferred embodiments, the ratio of shellac to zein in the combination ranges between about 7:1 to about 14:1, on a weight/weight basis.

It is unexpected that a coating composition base on a zein-shellac admixture will produce a coating which resists disintegration in the gastro-intestinal tract for periods ranging from about 25 minutes to up to 8 hours. Both zein and shellac are recognized for use in enteric coatings where resistance to disintegration in the stomach is desired. However, such coatings are unpredictable in their behavior and in many instances do not disintegrate until the capsule or tablet has reached the patient's colon, at which point release of the medicinal substance is ineffective.

Although it is not understood, it is believed that the shellac is modified by the zein so that the resulting coating is disintegratable both in the gastric and intestinal tracts at a predictable and reproducible rate. The total time of disintegration of a coating is readily determined and controlled by the amount of coating material applied to the particle.

Pharmaceutically acceptable plasticizers may also be incorporated in the coating composition for the purpose of improving the toughness, flexibility and handling characteristics of the finished coating. Such plasticizers include the mono- and di-alkyl esters of phthalate acid, such as for example, dibutyl phthalate and glycol and glyceryl esters, for example, triethylene glycol diproprionate, triacetone, castor oil, and the like.

It is also highly preferred to incorporate minor proportions of disintegration modifiers in the coating composition when the composition is being adapted to resist disintegration for a substantial period of time, on the order of 4 to 8 hours. These modifiers are materials which are pharmaceutically acceptable and which are known for their ability to withstand dissolution in the low pH environment of the stomach, but which are soluble in the intestinal tract. The addition of minor proportions of these materials permits the use of less coating material for a given period of disintegration resistance. For this purpose, it is preferred to utilize ethers and esters of cellulose such as, for example, cellulose acetate, cellulose acetate phthalate, and ethyl cellulose, or waxy materials, such as, for example, Japan wax, bees wax, paraffin and carnauba wax. In addition, polyvinyl compounds, such as polyvinyl alcohol, polyvinyl acetate, polyvinyl pyrrolidone and the like are useful as disintegration modifiers in accordance with the present invention. It should be clear, however, that the zein and shellac combination is useful without disintegration modifiers although the thickness of the coating required for a given period of disintegration resistance is greater than when the disintegration modifier is incorporated in the coating composition.

The coating composition of the present invention is conveniently applied to the particles by dissolving the coating substance in a suitable solvent. Due to the solubilities of zein and shellac, a highly preferred solvent for the coating composition is a dilute alcohol solvent, for example a 45 weight percent solution of ethyl alcohol. Aqueous isopropyl alcohol solvents may also be used, however, methanol solvents should be avoided as zein is unstable in methanol. The preferred solvent for the composition is a 45% ethyl alcohol in water solution since both the zein and the shellac are soluble therein.

The coating is applied by placing the particles to be coated in a rotating coating pan and adding sufficient coating solution to cover the particles. The particles are dried to remove the alcohol and water and the procedure repeated as often as necessary to produce a coat which resists disintegration in gastric or intestinal fluids for a desired period of time. Time of disintegration for a coating is determined using the standard procedure of the U.S. Pharmacopoeia.

Groups of particles having coatings which disintegrate at different times are combined in capsules or tablet form so as to produce a therapeutic preparation which will release a unit dose of therapeutic material at prescribed times after ingestion of the preparation. In the preferred embodiment, a first group of particles is included for release of therapeutic materials in the stomach in about 25 minutes after ingestion. The first group of particles may be coated or uncoated in accordance with this invention. A second group of particles is provided with a coating which resists disintegration for a period of about 2 hours, whereupon a second unit dose of therapeutic material is released in the intestine of the patient. A third group of particles is included for release of a unit dose of therapeutic material in a period of about 8 hours after ingestion of the preparation.

As has been pointed out, the nature of the therapeutic material is not critical and the coating composition of the preparation of this invention is compatible with any orally administrable medicinal substance. Likewise, the precise thickness of the coatings is not crtical and the coating composition is applied until the coating of the particle resists disintegration in gastric or intestinal fluids for a selected period of time. As a practical matter, it has been found that it is not necessary to check the particles after each application of the coating solution after having once determined the number of applications of the coating solution required to produce a coating which will resist disintegration for a selected period of time. Also, it should be noted that if excess coating is accidently or mistakenly applied to a group of particles, a portion of the coating can be removed by contacting the particles with the alcohol in water solution without harming the particles or the therapeutic material contained therein.

The following examples are by way of illustration of the preferred embodiments of the therapeutic preparation of the present invention and its manner of preparation.

EXAMPLE I

40 Kg of neutral particles (50 weight percent starch — 50 weight percent sugar pellets) having a 24 mesh particle size were placed in a 42 inch coating pan. The pan was rotated at between 28 and 30 rpm and 500 cc of a simple syrup solution containing 10 grams of digitoxin were distributed over the particles. Following addition of the digitoxin solution, the particles were dried in warm air and assayed for digitoxin content per particle.

The digitoxin containing particles were weighed and one third of the particles, on a weight basis, were set aside and identified as group I particles. The remaining quantity of particles were replaced in the 42 inch coating pan.

A coating solution was prepared in accordance with the following formula:

COMPOSITION A

| | |
|---|---|
| Zein, 10 weight percent in alcohol | 2000 cc. |
| Shellac (6 pound cut) | 2000 cc. |
| Ethyl cellulose, 2 weight percent in alcohol | 1000 cc. |
| Bees wax | 2 gm. |
| Castor Oil | 10 cc. |

The alcohol solvent utilized was 45 volume percent ethyl alcohol in water. The coating pan was set in rotation and a sufficient portion of the coating solution to cover the particles was distributed over the particles in the revolving coating pan. The particles were then dried in hot air until traces of the coating solution had disappeared and the particles were freely flowing in the pan.

This procedure was repeated an additional seven times to build up the coating on the particles. The coated particles were weighed and one half of the particles on a weight basis were separated and identified as group II particles.

The remaining particles were returned to the 42 inch revolving coating pan and the coating procedure repeated as set forth above using the following coating compositions:

COMPOSITION B

| | |
|---|---|
| Zein, 10 weight percent in alcohol | 2000 cc. |
| Shellac (6 pound cut) | 2000 cc. |
| Ethyl cellulose 2 weight percent in alcohol | 1000 cc. |
| Polyvinylpyrrolidone, 10 weight percent in alcohol | 1000 cc. |
| Bees wax | 5 gm. |
| Dibutyl phthalate | 5 cc. |

Ten applications of the coating solution were applied to the particles in the manner described above. These particles were identified as group III particles.

A sufficient number of particles to provide a 0.1 milligram dose of digitoxin were selected from each of the groups I, II and III particles and placed in a number 0 gelatin capsule. The capsule contained a total dosage of 0.3 milligrams of digitoxin.

The capsule was subjected to a disintegration test in accordance with the U.S. Pharmacopoeia. In accordance with this test the capsule was first placed in simulated gastric juice and maintained therein for a period of one hour with constant shaking. The gastric juice was prepared by dissolving 7.0 ml of hydrochloric acid U.S.P., 2.0 gm of sodium chloride and 3.2 gm pepsin U.S.P. in sufficient distilled water to make one liter (pH approximately 1.2). The simulated gastric juice was maintained at a temperature of 37°C. Following this period the remaining particles were removed from the simulated gastric juice and 100 cc of the gastric juice was extracted and assayed for digitoxin content in accordance with the method described in the U.S. Pharmacopoeia.

The remaining pellets were then placed in simulated intestinal juice and shaken for a period of three hours. The intestinal juice was prepared by adding 10.0 gm of pancreatin U.S.P. to a mixture of 250 ml of 5 molar potassium biphosphate, 190 ml of 5 molar sodium hydroxide and 460 ml of distilled water. The pH was adjusted to 7.5 and sufficient distilled water was added to make one liter. At the end of the 3 hour test period 100 cc of the intestinal juice was extracted and assayed for digitoxin content. The test was continued for an additional four hours and a second 100 cc was extracted assayed for digitoxin content.

In accordance with the test results, it was determined that the capsule had released 0.1 mg of digitoxin in the gastric juice at the end of one hour, 0.1 mg digitoxin at the end of four hours of testing and 0.1 mg of digitoxin was released after 8 hours of testing.

EXAMPLE II

Neutral particles of the type used in Example I were coated with the following vitamin preparation.

| | |
|---|---|
| Thiamine HCL (Vitamin B-1) | 400 gm |
| Riboflavin (Vitamin B-2) | 320 gm |
| Pyridoxine (Vitamin B-6) | 400 gm |
| Vitamin B-12 | 400 ml |
| Vitamin C | 20 kg |

The neutral particles were placed in the 42 inch rotary coating pan utilized in Example I and wetted with approximately 500 cc of the following coating solution:

| | |
|---|---|
| Zein solution, 5% in dilute alcohol | 1000 cc |
| Shellac (6 pound cut) | 100 cc |
| Castor Oil | 10 cc |
| Alcohol | 10 cc |

The solvent was 45 vol. percent ethyl alcohol in water.

Vitamin B-1 was applied by dusting the particles and the particles were dried in air while maintaining the pan rotation. Two more applications of the coating solution were applied over the dusted particles and the coatings were allowed to dry between each application.

Following the above procedure, the particles were dusted with the Vitamins B-2, B-12 and C in that order with each of the layers of vitamins being separated by a coating formed by two applications of the coating solution.

The finished particles were weighed and samples taken to determine the vitamin content per particle and to determine the disintegration time of the coatings in simulated gastric juice following the procedure described in Example I. It was determined that the vitamin content of the particles was released in a period of between about 25 minutes and 1 hour with the vitamin C being released first.

One third of the particles, on a weight basis were separated and identified as Group I particles. The remaining two-thirds were coated with 8 applications of the coating composition A of Example I following the procedure of Example I. One half of the coated particles were separated and identified as Group II particles and the remaining particles were coated with 10 applications of the coating composition B of Example I.

The Group I, II and III particles were thoroughly blended together and the blended particles placed in number 0 gelatin capsules. Approximately 500 mg of particles, based on the weight of the particles before coating with compositions A and B, were placed in each of the capsules to provide the following total dosage per capsule:

| | |
|---|---|
| Thiamine HCL (Vitamin B-1) | 5 mg |
| Riboflavin (Vitamin B-2) | 4 mg |
| Pyridoxine (Vitamin B-6) | 5 mg |
| Vitamin B-12 | 10 mcg |
| Vitamin C | 240 mg |

Capsules were tested for disintegration in simulated gastric juice and simulated intestinal juice following the procedures of the official U.S. Pharmacopoeia method as described in Example I. The test results showed that one-third of the total vitamin dosage was released in the gastric juice within 1 hour, a second one-third of the total vitamin dosage was released in the simulated intestinal fluid at the end of 4 hours and the remaining third was released by 8 hours.

EXAMPLE III

Sedative capsules were prepared in accordance with the method of Example I except that phenobarbital U.S.P. was substituted in place of the digitoxin of Example I. The capsules contained Group I, II and III particles with the unit dose of each group of particles per capsule being 30 mg of the sedative.

It will be evident that, while specific embodiments of the invention have been illustrated and described, various modifications and changes may be made without departing from the spirit and scope of the invention.

I claim:

1. A therapeutic preparation comprising a pharmaceutical gelatin capsule containing a blend of three groups of particles containing a pharmaceutically active material, said first group containing a unit dose amount of said material for release thereof within a period of one hour after ingestion, a second group of said particles containing a unit dose amount of said material being provided with a coating comprising a major proportion of zein and shellac in a weight/weight ratio of between 1:7 and about 1:14 and minor proportions of ethyl cullulose, bees wax and a plasticizer, said coating having an effective thickness for disintegration and relase of said material in a period of about 4 hours after ingestion, and a third group of said particles containing a unit dose amount of said material being provided with a coating comprising a major proportion of zein and shellac in a weight/weight ratio of between about 1:7 and about 1:14 and minor proportions of ethyl cellulose, bees wax, polyvinylpyrrolidone and a plasticizer, said coating having an effective thickness for disintegration and relase of said material in about a period of about 8 hours after ingestion.

2. The therapeutic preparation of claim 1 wherein said pharmaceutically active material is digitoxin.

* * * * *